United States Patent [19]

McFarland et al.

[11] Patent Number: 4,770,298

[45] Date of Patent: Sep. 13, 1988

[54] PACKAGING OF ABSORBENT PRODUCTS

[75] Inventors: Timothy M. McFarland, Winnebago County; Arthur E. Garavaglia, Outagamie County, both of Wis.

[73] Assignee: Kimberly-Clark Corporation, Neenah, Wis.

[21] Appl. No.: 835,016

[22] Filed: Feb. 28, 1986

Related U.S. Application Data

[62] Division of Ser. No. 672,017, Nov. 16, 1984.

[51] Int. Cl.$^4$ ............................................. B65D 85/66
[52] U.S. Cl. ..................................... 206/390; 206/440
[58] Field of Search .......................... 206/390, 440, 438

[56] References Cited

U.S. PATENT DOCUMENTS

| | | | |
|---|---|---|---|
| 2,898,928 | 3/1959 | Ivy | 206/390 |
| 3,225,918 | 12/1965 | Mines | 206/390 |
| 3,386,619 | 6/1968 | Douglas | 206/390 |
| 3,613,142 | 10/1971 | Chaney, Jr. | 206/390 |
| 3,674,614 | 7/1972 | Templeton | 206/390 |
| 3,710,396 | 1/1973 | Tomlinson | 206/390 |
| 3,958,768 | 5/1976 | Fairbanks | 206/390 |
| 4,016,975 | 4/1977 | Hammer | 206/390 |
| 4,658,962 | 4/1987 | Burns et al. | 206/390 |
| 4,677,697 | 7/1987 | Hayes | 206/390 |

FOREIGN PATENT DOCUMENTS

| | | | |
|---|---|---|---|
| 537510 | 5/1955 | Belgium | 206/390 |
| 1035329 | 7/1978 | Canada . | |
| 1111387 | 10/1981 | Canada . | |

Primary Examiner—Joseph Man-Fu Moy
Attorney, Agent, or Firm—Paul A. Leipold

[57] ABSTRACT

The invention provides the combination of a dispenser and a series of incontinent or catamenial pads that are connected by easily severably areas. These pads may be rolled without harmful effects to the pad. The rolled pads that are connected by severably means are suitable for combination with a dispensing container that allows them to be withdrawn a single pad at a time.

In a particularly preferred embodiment an incontinent pad having elasticized edges and double baffle is connected in series by severably portions at the ends. The pad is placed into a generally cubical box and withdrawn either from the center of the roll at the top of the box or from the end of the roll at the side of the box. The container is provided with a removable section at either the top or side for the withdrawl of pads.

12 Claims, 6 Drawing Sheets

PACKAGING OF ABSORBENT PRODUCTS

This is a divisional of copending application Ser. No. 672,017, filed on Nov. 16, 1984.

TECHNICAL FIELD

This invention relates to disposable absorbent pads. It particularly relates to disposable incontinence pads and catamenial pads and their packaging.

BACKGROUND

Disposable absorbent articles are well known and have many uses. For example, disposable diapers are intended to absorb and contain urine. Bandages are intended to absorb and contain blood and other body exudates, while catamenial pads are intended to absorb and retain menstrual fluids. In each instance, the disposable absorbent article absorbs and retains a liquid, thereby preventing that liquid from soiling, wetting, or otherwise contaminating the vicinity surrounding the point of liquid discharge. For example, U.S. Pat. No. Re. 26,151 which issued on Jan. 31, 1967 to R. C. Duncan et al. entitled "Disposable Diaper" teaches a disposable diaper intended to absorb urine and prevent the wetting of the wearer's clothing.

Disposable absorbent articles perform without leaking, and several concepts have been proposed to improve the liquid containment characteristics of disposable absorbent articles such as disposable diapers. U.S. Pat. No. 3,999,548 entitled "Disposable Diaper Having Fluid Trap" which issued to J. Hernandenz on Dec. 28, 1976 teaches that the liquid containment characteristics of a diaper can be improved by securing sealing strips of waterproof material to the face sheet of the diaper. Alternatively, U.S. Pat. No. 3,860,003 entitled "Contractible Side Portions For a Disposable Diaper" which issued to K. B. Buell on Jan. 14, 1975 and U.S. Pat. No. 4,050,462 entitled "Disposable Diaper With Elastically Constricted Crotch Section" which issued to L. S. Woon et al. on Sept. 7, 1977 both teach a concept for reducing liquid leakage which involves providing an elastic member in a disposable diaper. The elastic member is positioned so that when the diaper is worn, the diaper is drawn snugly about the legs of the wearer. The elastic causes the diaper to form a seal about the leg of the wearer thereby preventing liquid from leaking out of the diaper.

While diaper formation techniques are well developed, the formation of pads for incontinence uses has not resulted in as effective a garment. The shaping techniques of diaper formation have not produced effective incontinence garments. The adult body is shaped differently and has different liquid capacity requirements and fit problems than the infant.

Many articles used as incontinent products for mild incontinence or for menstrual pads have been found unsatisfactory as they are bulky and/or ineffective. Many such garments are formed by forming flat sheets into a diaperlike structure for incontinent use. Other pads for catamenial use have been formed in thin flat structures, but these structures have been low in absorption. Further, flat structures have a tendency to wrinkle between the legs during use causing discomfort and distorting the target area where the exudate will be located causing leakage.

Small elasticized pads have been proposed, such as in U.S. Pat. No. 3,371,668, to Johnson in which an elasticized sanitary napkin is disclosed. The sanitary napkin has elastic threads that are imbedded in the napkin, running in the long direction of the napkin. Another small elasticized pad has been proposed in European Patent application No. 0.091,412, of Nedestam in which a sanitary napkin having elasticized edges and a raised center portion is disclosed. However, these pads have not found wide acceptance as they are bulky and do not fit the female form to provide both comfort and absorbency.

The U.K. patent application No. GB 2,103,093 of Blaney discloses a diaper structure having elasticized flaps that are adapted to fit to the legs of the diaper wearer and minimize leakage. The flaps are formed at the edges of a diaper and exert a contact pressure on the skin of the leg when the diaper is fastened in place. There has been proposed in U.S. Pat. No. 4,182,334 - Johnson, a perineal shield device for containment of discharge caused by incontinence. While this device has been effective, there still are leakage problems that occur. The leakage problem is particularly acute in instances where there is rapid discharge of urine that may leak from the pad prior to being absorbed.

The devices such as those of U.S. Pat. No. 4,182,334 - Johnson, and those in the U.S. Pat. No. 4,315,508 - Bolick as well as other shaped pads present difficulty in packaging. These pads having a particular fold and shape adapted to conform to the body must be loosely packaged in large boxes to avoid creasing and permanent deformation of the incontinence devices. Creases and deformation from the intended shape is detrimental to their effectiveness.

There remains a need for a incontinence device that may be conveniently, economically and discretely packaged.

DISCLOSURE OF THE INVENTION

An object of the invention is to overcome disadvantages of prior incontinent and catamenial pad packaging and dispensing devices and methods.

Another object of this invention is to form a compact, sanitary dispenser of catamenial and incontinence pads.

An additional object of this invention is to create convenient dispensing of incontinence pads.

These and other objects of the invention are generally accomplished by providing the combination of a series of incontinent or catamenial pads that are connected by easily severable areas with a container for dispensing the pads. These pads may be rolled without harmful effects to the pad. The rolled pads that are connected by severable means are suitable for combination with a dispensing container that allows them to be withdrawn a single pad at a time.

In a particularly preferred embodiment an incontinent pad having elasticized edges and a double baffle is connected in series by severable portions at the ends. The pad is placed into a generally cubical box and withdrawn either from the center of the roll at the top of the box or from the end of the roll at the side of the box. The container is provided with a removable section at either the top or side for the withdrawal of pads.

MODES FOR CARRYING OUT THE INVENTION

The pad suitable for dispensing in accordance with the invention offers numerous advantages over the prior art pads for mild urinary incontinence and catamenial use. The pad preferably dispensed for the invention is comfortable to wear and not deformed by rolling. The pad further is low cost in formation as it is generally rectangular and is formed of conventional materials. The pad further has the advantage that the dual baffle arrangement provides greater protection against the leakage of urine, particularly during rapid discharge when the urine may not all be immediately absorbable. The pad further is comfortable and nonobtrusive, even though having a relatively large moisture-absorption capability. These and other advantages of the preferred pad for dispensing in the invention will be apparent from the detailed description below, particularly with view to the description of the drawings.

Another advantage of the pad and dispenser of the invention is that the pad when formed with heat shrinkable elastic may be wrapped on a core after forming and prior to heat shrinking of the elastic. The unshrunken roll of pads may then be placed into the dispensing box prior to heat activation. It is even possible that the pads could be sold to the consumer in the unshrunken condition and the shrinkable elastic activated in the home by use of hot air from a hair dryer or in an oven or other home-heating device. This would even let the user control the fit by heating a controlled amount to control shrink and thereby control the fit. Other advantages in having the consumer shrink the pad are that elastic fatigue and loss of elasticization that occur during storage are prevented. Further, manufacturing costs are lower as the equipment and power necessary to shrink are unnecessary to the manufacture.

The pad having dual baffle is particularly preferred for the dispensing means of the invention. The pad is suitable for rolling to form a compact roll of pads that when unrolled will asuume a utilitary shape and not be deformed by the rolling, unrolling, and dispensing. Further the pad itself is particularly suitable for being formed in the rolled shape, thereby minimizing processing after formation. The dispenser of the invention is particularly advantageous as it allows sanitary, discrete dispensing of catamenial and incontinence pads.

Figure 1:
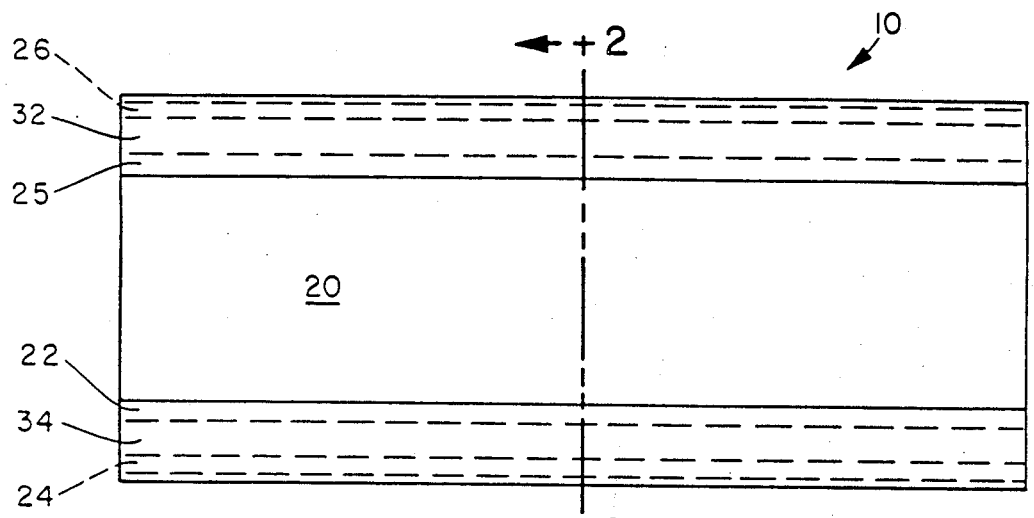
FIG. 1 is a plan view of a pad suitable for dispensing in accordance with the invention.
Figure 2:
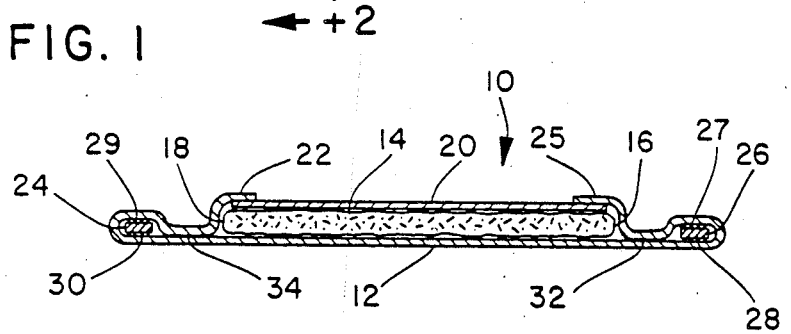
FIG. 2 is a cross-section of the pad of FIG. 1 taken on line 2—2 of FIG. 1.

FIG. 1 illustrates in plan view a pad suitable for the invention. The pad of the invention in FIG. 1 is shown in cross-section in FIG. 2. The pad 10 is composed of a impervious backing sheet 12 that extends beyond the edges 16 and 18 of absorbent layer 14. The absorbent material is covered by a permeable web 20 to which the impervious backing sheet is attached at 2 and 24. In the folded portion beyond the edges 16 and 18 of the absorbent material the impervious backing sheet is folded over elastics 24 and 26 that are adhesively connected to the backing sheet below the elastics at 28 and 30 and above the elastics at 27 and 29. The backing sheet is further adhered to itself in the portions 32 and 34 that are located between the elastics 24 and 26 and the edges of the absorbent 16 and 18. The backing sheet 12 is adhered to the permeable web 20 and also preferably to absorbent 16 at 22 and 25. The portion outside the absorbent where the backing sheet is adhered to itself or surrounds the elastic form the upstanding baffle when the elastic contracts. The views of FIG. 1 and 2 are with the elastics 24 and 26 in extended condition.

Figure 3:
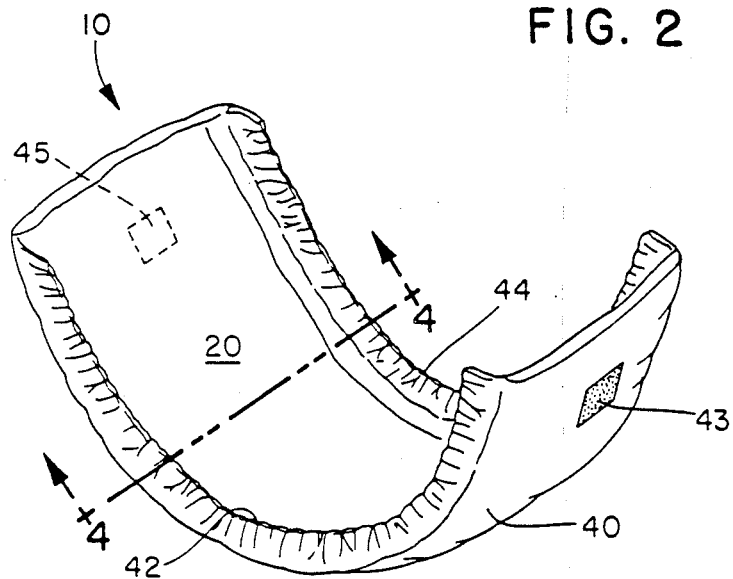
FIG. 3 is a perspective view of the pad of FIG. 1.
Figure 4:
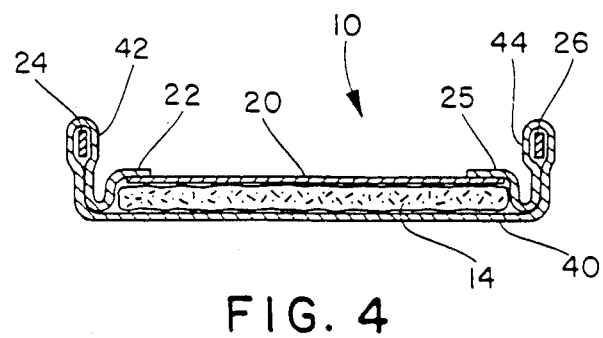
FIG. 4 is a cross-section along line 4—4 of FIG. 3.

The perspective view of FIG. 3 and cross-sectional view of FIG. 4 illustrate the pad preferred in the dispenser combination of the invention that has been allowed to assume the shape that results when the elastics 24 and 26 relax and contract. It is noted that the bottom 40 of the pad in the preferred embodiment is generally smooth and ungathered with the upstanding baffles 42 and 44 forming a trough-like member with a generally smooth and ungathered bottom 40 and generally vertical sides forming the upstanding baffles 42 and 44. It can be seen that the structure has baffles 22 and 24 that inhibit the movement of moisture from within or below the absorbent around the edges of the absorbent to the surface of the pad. The upstanding baffles 42 and 44 further inhibit motion of the liquid that is on the surface of the pad as well as tending to seal the pad against the perineal region of the wearer.

The bowed shape of the pad in combination with the unstanding baffles 42 and 44 is believed to result in the superior fit and leak-resistance of the pad. Further, the elastics 24 and 26 not being under tension when the garment is worn allow easy deformation of the edges of the garment to conform with bodily shape or adjust for movement.

Figure 5:
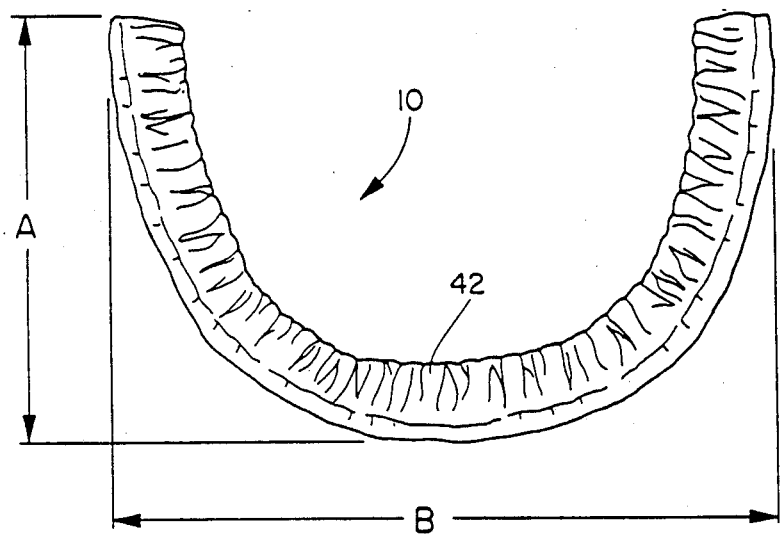
FIG. 5 is a view showing the height and length relationship of the pad suitable for the dispenser of the invention.

The illustration of FIG. 5 shows the bowed pad in relaxed state. The bowed height of the pad is indicated as "A". The bowed length is indicated as "B." The bowed height "A" of the pad of the invention is typically between about 0.5 and about 5 inches in height. A preferred range of "A" is between about 2.5 and about 3.5 inches for fit of the typical woman. The bowed length "B" may be typically between about 6.5 and about 12 inches. The preferred bowed length is about 7.5 to about 8 inches to fit the average woman. The ratio of the bowed height to bowed length is about 2 or 3 for a pad of a comfortable fit with good leak resistance.

As stated above, it is preferred in the pad for the dispenser of the instant invention that the bottom of the pad 40 be generally smooth and ungathered while the upstanding baffles 42 and 44 be generally perpendicular to the bottom of the pad. In a preferred method of forming the pad in order to accomplish this structure, the pad is formed using a heat-shrinkable elastic such as that disclosed in co-pending commonly assigned Ser. No. 606,082, filed May 1, 1984, Matray et al. hereby incorporated by reference. Other known heat-shrinkable elastic strip materials such as those in Raychem's U.S. Pat. No. 3,636,917 also may be utilized.

Figure 6:
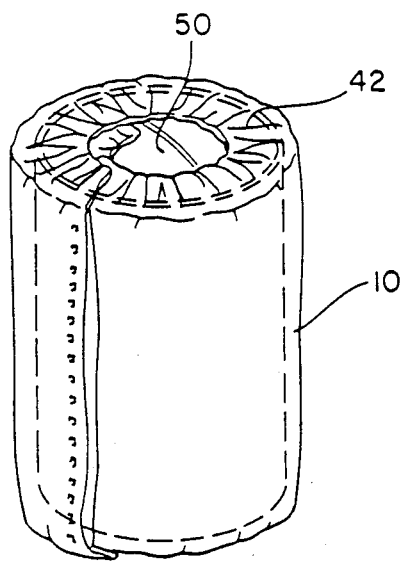
FIG. 6 is a view of a pad cured on a roll.
Figure 7:
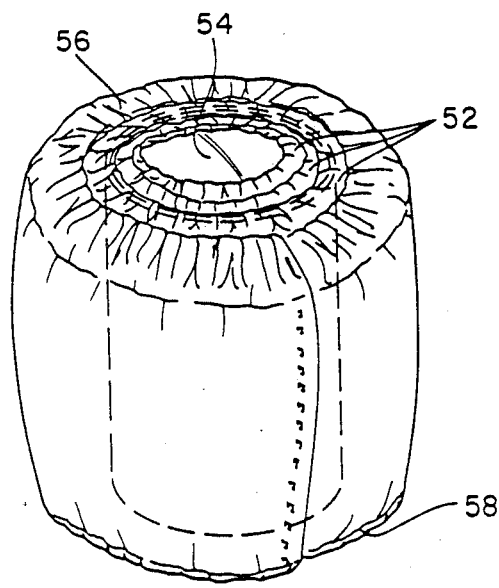
FIG. 7 is a view of a roll of pads that have been cured simultaneously.

FIG. 6 illustrates a preferred forming technique to produce a dispensable pad and to best obtain the generally smooth and ungathered bottom portion 40 in combination with the raised flaps 44 and 42. As illustrated in FIG. 6, the pad 10 is wrapped onto core 50. The core 50 may be formed of a cardboard roll such as used in toilet paper rolls. After the pad with the elastic in unshrunken condition is wrapped onto the core, the pad is subjected to heat at the elastic-containing end portions in order to bring about shrinkage and form the flaps 42. As illustrated in FIG. 7, it is preferred for the invention to wrap a series of pads 52 around a core 54 such that a group of the pads may be heated together to shrink the elastic at the ends 56 and 58 of the pad roll. Shrinking on a core is the preferred method as the pads that result have a smoother bottom and more vertical sides than those not shrunk while rolled on a form. It is also preferred as a compact roll of pads is formed that fits a dispenser without further treatment. The means of applying heat to shrink the heat-shrinkable elastic may be any suitable means. Suitable heating means are those such as hot air or microwave heating. The shrinking may be carried out either with heat shrinking prior to placing in the dispenser or shrinking after placing in the dipsenser. The shrinking can be performed by the consumer or at the manufacturing site. While illustrated with forming on a rigid cardboard roll it is also possible to form on an inflatable or collapsible core when use of the roll of pads by dispensing from the center of the roll is desired.

Nevertheless, it is also possible to form the pads suitable for the dipsensers of the invention with stretched elastic which will cause the pad to immediately assume the bowed shape when the stretched elastic is relaxed. Pads formed by this method, as they are not shrunk over a form, have a more rounded bottom than the preferred pads, but nevertheless form a double-baffle system providing comfort to the wearer. It is theorized that in the preferred embodiment the flat bottom is more likely to bend upward against the genital region when it is worn. By bending upward against the genital region, the urine or menstrual flow will contact the pad immediately on being exuded and is more likely to be absorbed prior to spreading or leaking from the edge of the pad.

Figure 8:
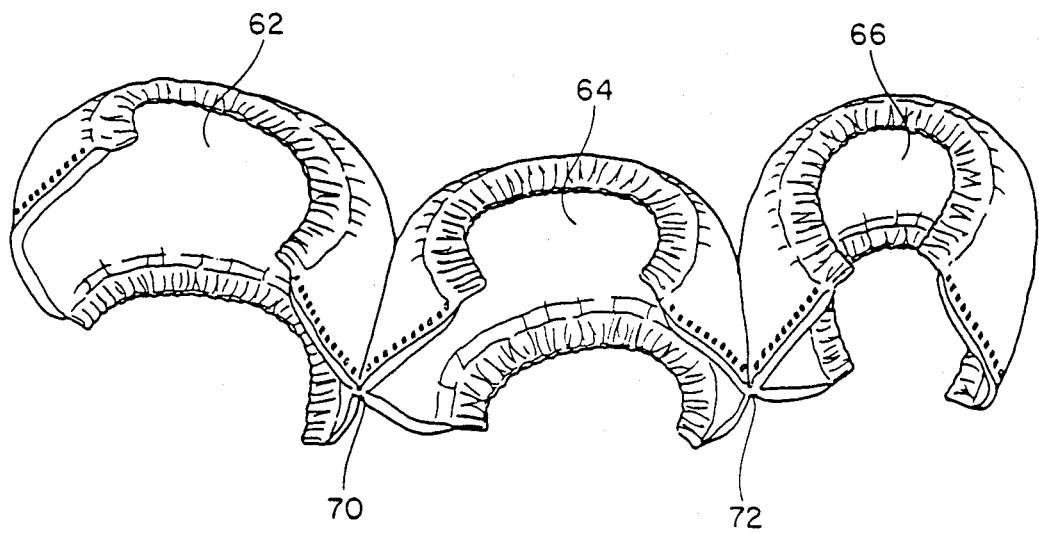
FIG. 8 is a group of pads that are connected.

Illustrated in FIG. 8 is a series of the pads of the invention indicated as pads 62, 64, and 66. The pads are joined by small portions of the impervious backing sheet at 70 and 72. These sheets if desired may be detached prior to being packaged for sale.

Figure 9:
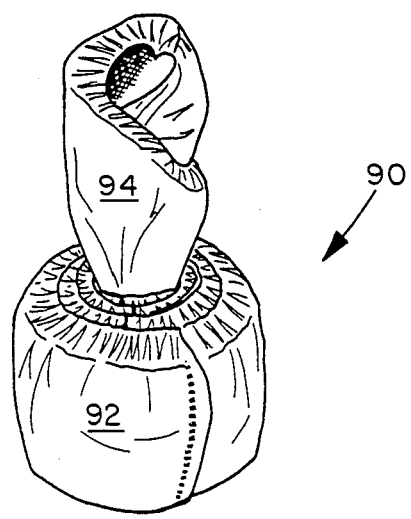
FIG. 9 is a roll of pads with one pad being withdrawn from a the middle of the roll.
Figure 10:
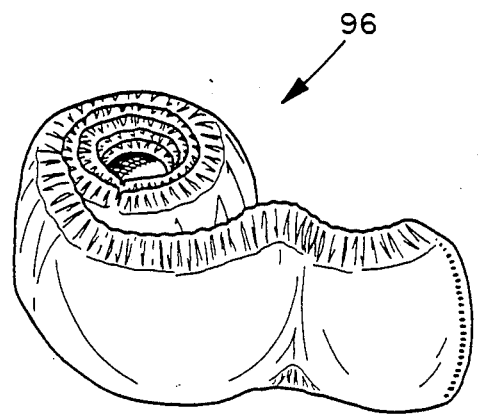
FIG. 10 is a roll of pads with one being withdrawn from the side of the roll.
Figure 11:
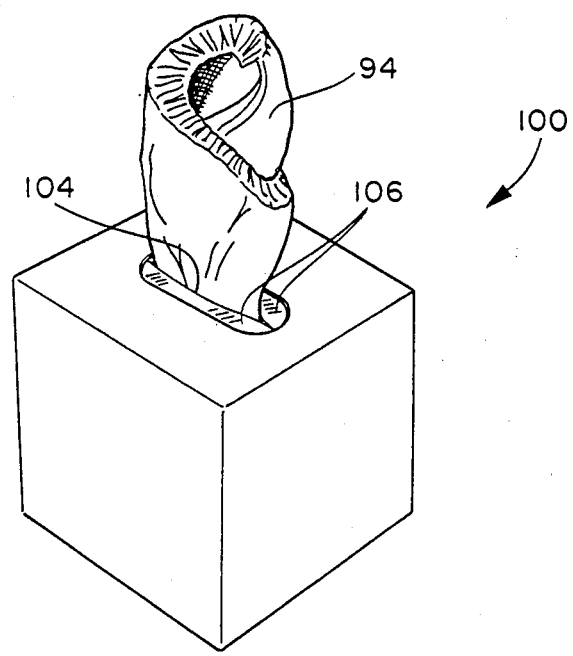
FIG. 11 is a combination of the invention in which a pad is drawn from the top of the container and the inside of the roll.
Figure 12:
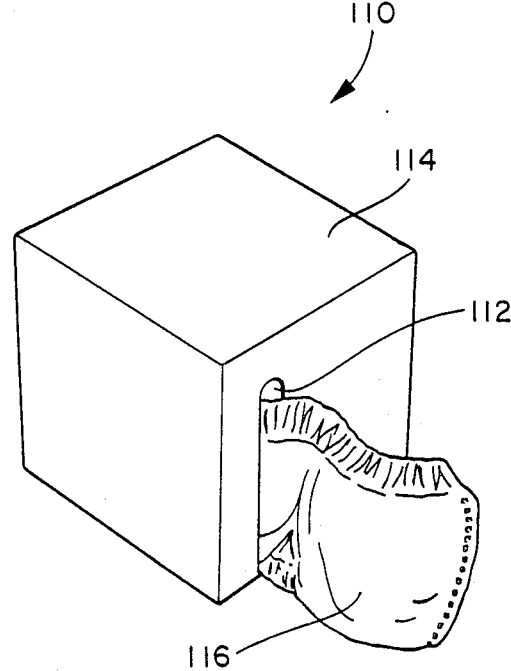
FIG. 12 is a dispenser combination of the invention in which the pad is withdrawn from the outer portion of the roll.

FIGS. 9, 10, 11, and 12 illustrate packaging means and the rolls of incontinent garments to be placed in the packages in accordance with the invention. In FIG. 9 the roll 90 is composed of individual pads 92 and 94. These pads are rolled or formed as a roll from which the inner pad 94 may be withdrawn. These pads as earlier stated may be formed on an expandable or mechanically collapsible mandrel. Such mandrels, not shown, are well known and may be expanded and contracted either mechanically or by inflation and deflation during forming. The roll 96 of FIG. 10 is also formed on a core that may be left in the roll after winding the pads on the roll or the winding and later heat-shrinking of the elastic upon the core. The roll 92 of FIG. 9 is particularly suitable for use with the FIG. 11 dispenser 100 wherein a pad 94 may be withdrawn from a slot 104. The slot 104 may be guarded by a pair of flexible flat polymer sheet members 106 that prevent dust from entering the box. The roll of FIG. 10 may suitably be dispensed from a dispenser 110 of FIG. 12. As shown in FIG. 12, the dispenser contains a roll that is dispensed from a slot 112, that forms a vertical hole on the side of the box 114.

The roll of pads that is withdrawn from the dispenser 100 and 110 may be suitable connected by any means. The pads may be carried by tape that is severed between the pads during dispensing. Further, they may be separated by perforations between separate pads. Or as shown in FIG. 8, they may be connected by a single segment of the polymer backing material that is severed between the pads during dispensing. The single segment of backing material allows better shaping of each pad without deformation caused by the shrinkage of the pad to which it is connected. It also is suitable that packages could be arranged to dispense individually-wrapped pads where the packages are connected in series. The pads earlier described in the description of FIGS. 1–5 are particularly suitable for packaging or for dispensing from roller dispensers.

In the dispensing of hygienic articles such as incontinence pads and catamenial pads it may be desirable that the pads be protected so that dust and other airborne materials do not contaminate them. Therefore it may be desirable that the dispenser be provided with sealing flaps in the slot 112 or 104 from which the pads are dispensed. Such flaps may take the form of opposed overlapping polymer films that prevent dust from entering the dispenser. Typical of materials for forming the polymer films are polyethylene and polyvinyl chloride films.

Figure 13:
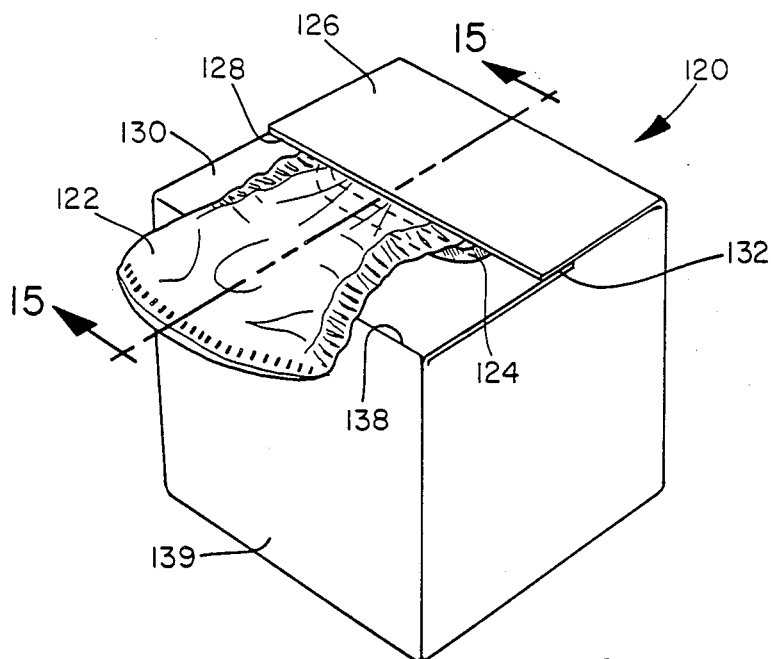
FIGS. 13 and 14 are alternative dispensers in accordance with the invention.
Figure 14:
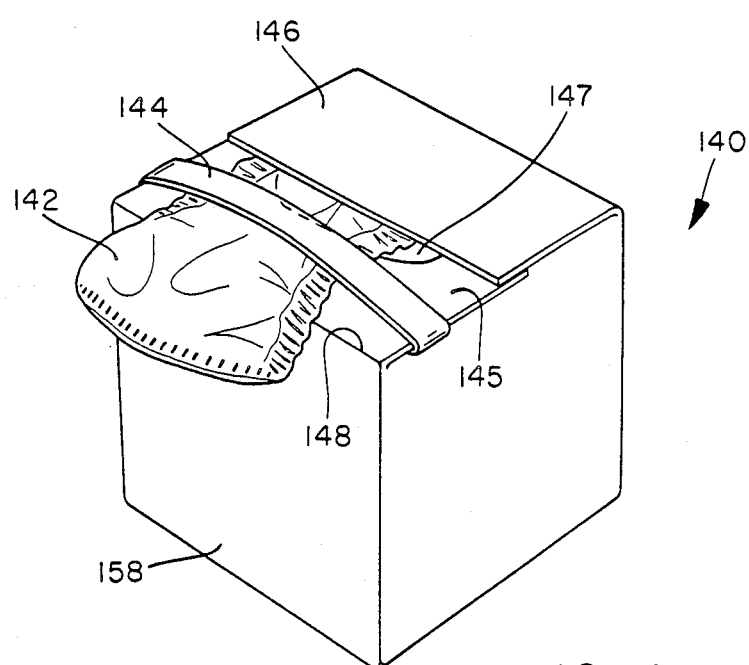
Figure 15:
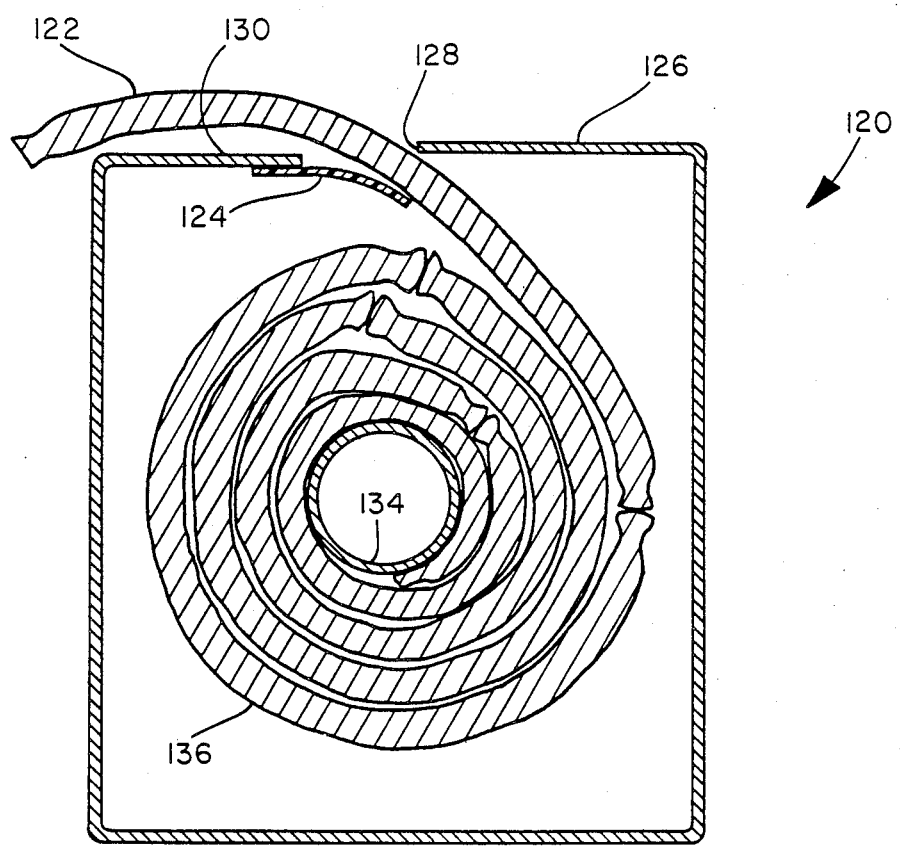
FIG. 15 is a cross-section of the dispenser of FIG. 13 on line 15—15.

FIGS. 13–15 illustrate alternative dispensers that are believed to provide better dust protection for the roll of pads in the container. The receptacle 120 of FIGS. 13 and 15 is provided with overlapping flaps 130 and 126 forming overlap area 132. The pad 122 is drawn from below flap 126 and over flap 130. Flap 130 is partially cut away and provided with a polymer sheet 124 that is flexible and preferably somewhat elastic such that it will conform to the bottom of pad 122 and exclude dust from the container. Generally a polymer sheet material such as a film of polyethylene would be suitable. The pad 122 may be pulled from receptacle 120 and separated from the pads to which it is attached by pulling against edge 128 of flap 126 or against the edge 138 where flap 130 and vertical side 139 meet.

In the embodiment of FIG. 14 the receptacle 140 is similar to that of FIG. 13 with overlapping flaps 145 and 146. The flap 145 is provided with a cutout containing flexible polymer sheet 147. The pad 142 is pulled over sheet 147 and under strap 144. The strap 144 holds the body contacting side of pad 142 against flap 145 so it less likely to be dust contaminated. The pad is separated by pulling over edge 148 formed by the foldline of vertical side 158 and flap 145. The hold-down strap may be elastic, semirigid plastic, or cardboard.

The pads that may be dispensed from the combination of the invention can be of any desirable form. Suitable for the invention are those having elasticized edges, particularly those shaped to curl into a somewhat trough-like member that will not be extensively and adversely affected by rolling prior to dispensing. Typical of such pads are those such as disclosed in European Patent Application No. 0,091,412 to Widlund and European Pat. No. 0,098,512 - Beckestrom, both of which disclose pads suitable for incontinence use that have elasticized edges. Another pad suitable for use in combination with this invention is U.S. Ser. No. 629,297 - Damico et al. filed July 9, 1984 that discloses an incontinent or catamenial device that may have fully elasticized edges and assumes a trough-like configuration in use. Ser. No. 629,297 is co-assigned and hereby incorporated by reference. The preferred pad for the dispensing is the double-baffle pad described above and illustrated in FIGS. 1–5 having a generally smooth and ungathered bottom and vertical sides when shaped prior to use. Such a pad is particularly adapted for wrapping around a core with the upstanding edges extending beyond the core so as not to be deformed. Such a rolled or wrapped series of incontinent or catamenal pads is particularly adapted for the combination of pad and dispenser of the invention.

The impervious backing sheet of the pads used in the combination of the instant invention is impervious to liquids. It serves to prevent the soiling of the garments of the wearer by preventing the penetration of the moisture. It is possible that the material could be vapor permeable while being liquid-impermeable. The impervious backing sheet may be formed of any suitable plastic film. Typically such films are polyethylene films having a thickness of from 0.0005 to about 0.002 inches. A particularly preferred sheet is a co-extruded sheet of spunbonded polyethylene filaments with a sheet of polyethylene. The spunbonded material is placed on the exterior of the garment and is preferred as it is believed to provide added strength as well as providing a better feel, a cloth-like surface and is quieter when worn. Suitable co-extruded sheets are known in the art and available from Printpak Inc. such as the sheet marketed as No. 97-55508.

The pad's absorbent layer may be selected from any of the known absorbent materials for use in absorbent pads. Typical of such materials are the divellicated wood fibers, polyester fibers, cotton fibers, or other known absorbent fiber materials. A preferred material is the material commonly known as "coform." This material is an air-formed blend of meltblown polypropylene and divellicated wood fibers. A particularly preferred form has about 70 percent wood and about 30 percent polypropylene meltblown material. In an optimum form the coform material may be simultaneously combined with a superabsorbent as it is meltblown such as is disclosed in copending and co-assigned application, U.S. Ser. No. 60/602,993, filed Apr. 23, 1984, inventors T. McFarland and T. Lang, hereby incorporated by reference. Such a material is optimum as it has superabsorbent incorporated therein and is highly liquid-absorbent, but does not allow release of superabsorbent or present a slimy feel to the wearer.

The body-side liquid permeable web of the pad may be any compliant, soft-feeling, nonirritating and permeable material. Typical of such materials are a wide range of materials such as porous foams, apertured plastic films, natural fibers, synthetic fibers such as polyester, polypropylene, or a combination of natural and synthetic fibers. The body-side permeable layer serves to prevent contact of the pubic region of the wearer with the wet absorbent material. A preferred material has been found to be the spunbonded polypropylene liner material such as is known for diaper use. Another preferred material is the permeable web material that is formed with a transfer layer integrated to a nonwoven cover as disclosed in U.S. Pat. No. 4,397,644, Mathews et al. The body-side material may be treated with a wetting agent or surfactant to make it hydrophilic. The web also may be bonded to the coform layer. The bonding to the coform layer is believed to aid in passing of liquids through the permeable member rather than having them run along the surface. It is noted, however, that the dual baffle system of the preferred pad of the invention does serve to prevent overflowing of liquids running along the surface of the liner as the upstanding baffle will divert the liquid onto the absorbent surface prior to its passing over the side of the pad.

The pads dispensed by the combination of the invention may be any suitable size that will conform to the pubic region of the wearer. While the preferred pad has generally been discussed for use by women, it is also believed suitable for use by men, particularly in the larger sizes or with larger upstanding baffles. Generally, the range of width of the adsorbent is between about 2 and about 4 inches. A preferred width absorbent is about 3 inches so as to result in a pad of a width comfortable for most persons.

The height of upstanding baffles 42 and 44 of the preferred pad may be any suitable height that will give comfort and low leakage. Generally it is preferred that the baffles have a height between about one-half inch and five-eighths inch for a woman's pad that will be comfortable and provide good leakage protection. The baffle heights for men may be between about one inch and about one and one-half inch in order to provide contact with the periphery of the genital area while allowing room for the genitals.

The amount of the overlap of the impervious backing sheet 40 in area 22 and 24 over the absorbent 14 to form the lower baffle of the preferred pad may be selected to give good protection against leaking around the edges while at the same time not interfering with urine discharge into the pad. A preferred range of overlap of the absorbent by the backing material to form the lower baffle at areas 22 and 24 is a lower baffle of between about one-half inch and one-fourth inch width on each side so as to not interfere with urine discharge into the pad when it is formed but still retain the baffling effect of any liquid that is squeezed from the absorbent or has not yet been absorbed by the absorbent.

While the combination of the invention finds primary use in dispensing of incontinent or catamenial devices, it is possible that the device could find utility as a bandage for the elbow, knee or foot.

The preferred device for the dispenser of the invention used as an incontinent or catamenial pad may be worn inside tight-fitting underpants or may be held in place on the underpants by adhesive points 43 and 45 as shown in FIG. 3. Alternatively, one or a series of pressure-sensitive adhesive strips could be placed on the length of the pad and covered with a peel strip that would be removed prior to the garment being placed inside the underwear. It is preferred that adhesive area be located near the end such as shown in FIG. 3 as the suspension of the device from the ends seems to give better comfort and protection. The device also could be held in place by belt devices that are known in the art for use with menstrual pads.

In describing the present invention, certain embodiments have been used for purposes of illustration; however, other embodiments or modifications within the spirit and scope of the invention will readily occur to those skilled in the art after reading of this disclosure. The invention is accordingly not to be limited to the specific embodiments illustrated, but only in accordance with the appended claims.

We claim:

1. The combination of a series of catamenial or incontinence pads having at least partially elasticized edges, and a dispensing aid comprising a dispensing container, adapted to enclose a series of said pads, said container further provided with an opening for withdrawing a single pad; said pad being withdrawn from a roll of said pads connected in series wherein each pad in said series comprises an impervious backing sheet, an inner generally rectangular absorbent layer and a bodyside permeable web wherein said impervious backing extends beyond the long side of said rectangular absorbent layer and is folded back on each side and adhered to said permeable web and absorbent layer, and wherein elastic members are adhered within the folds of said impervious sheet and wherein said impervious sheet is adhered to itself in the areas of the folds between said elastic members and the edge of said absorbent, and wherein said series of pads is wrapped on a core about equal in length to the width of the pad's absorbent such that the upstanding elasticized edges of said pad are not deformed by the core.

2. The combination of claim 1 wherein the pads are withdrawn from the middle portion of said roll.

3. The combination of claim 1 wherein said pads are withdrawn from the outer portion of said roll.

4. The combination of claim 1 wherein said series of pads are wrapped around a core piece.

5. The combination of claim 1 wherein said container is generally cubical.

6. The combination of claim 1 wherein said opening is provided with dust-sealing flaps.

7. The combination of claim 1 wherein said pads are connected by a narrow piece of the impervious backing members of said paids.

8. The combination of claim 1 wherein said container is provided with a removable covering for said opening.

9. The combination of claim 1 wherein said opening is provided with at least one flexible polymer sheet as a dust shield.

10. The combination of claim 9 wherein said container has overlapping flaps and said opening is cut out in the end of the underlaying flap and the opening is covered with a flexible polymer sheet.

11. The combination of claim 10 further provided with a means to hold said single pad against said container as it is withdrawn.

12. The combination of claim 1 wherein said pads forming said roll are connected by easily severable areas.

* * * * *

UNITED STATES PATENT AND TRADEMARK OFFICE
CERTIFICATE OF CORRECTION

PATENT NO. : 4,770,298

DATED : September 13, 1988

INVENTOR(S) : Timothy M. McFarland and Arthur E. Garavaglia

It is certified that error appears in the above-identified patent and that said Letters Patent is hereby corrected as shown below:

IN THE SPECIFICATIONS:

Column 1, line 27, after "articles" insert --should--.

Column 1, line 32, delete "Hernandenz" and substitute therefor --Hernandez--.

Column 4, line 9, delete "2" and substitute therefor --22--.

Column 4, line 42, delete "unstanding" and substitute therefor --upstanding--.

Column 4, line 58, delete "or" and substitute therefor -- to --.

Column 5, line 27, delete "dipsenser" and substitute therefor --dispenser--.

Column 5, line 34, delete "dipsensers" and substitute therefor --dispensers--.

Column 8, line 17, delete "adsorbent" and substitute therefor --absorbent--.

Signed and Sealed this

Twenty-first Day of November, 1989

Attest:

JEFFREY M. SAMUELS

Attesting Officer     Acting Commissioner of Patents and Trademarks